United States Patent [19]

Akimoto et al.

[11] 4,371,533
[45] Feb. 1, 1983

[54] 4,5-DEOXYMAYTANSINOIDS, THEIR USE AND PHARMACEUTICAL COMPOSITIONS THEREOF

[75] Inventors: Hiroshi Akimoto; Akiyoshi Kawai, both of Kobe, Japan

[73] Assignee: Takeda Chemical Industries, Ltd., Osaka, Japan

[21] Appl. No.: 306,776

[22] Filed: Sep. 29, 1981

[30] Foreign Application Priority Data

Oct. 8, 1980 [JP] Japan .................. PCT/JP80/00240

[51] Int. Cl.³ .................. C07D 498/16; A61K 31/535
[52] U.S. Cl. .......................... 424/248.54; 424/248.51; 260/239.3 T; 260/239.3 P
[58] Field of Search ............... 260/239.3 T, 239.3 P; 424/248.54, 248.51

[56] References Cited

U.S. PATENT DOCUMENTS 4,162,940  7/1979  Higashide et al.

FOREIGN PATENT DOCUMENTS

| 4466  | 10/1979 | European Pat. Off. |
| 10735 | 5/1980  | European Pat. Off. |
| 11276 | 5/1980  | European Pat. Off. |
| 11277 | 5/1980  | European Pat. Off. |
| 11302 | 5/1980  | European Pat. Off. |
| 14402 | 8/1980  | European Pat. Off. |

OTHER PUBLICATIONS

Corey et al., "J. Am. Chem. Soc." vol. 102 (1980) pp. 6613–6615 (Oct. 8, 1980).
S. M. Kupchan, Journal of Medicinal Chemistry, 21(1), 31–37. (1978).
E. J. Corey et al., J. Am. Chem. Soc., 100(9), 2916 (1978).
E. J. Corey et al., J. Am. Chem. Soc., 102(4), 1439 (1980).

*Primary Examiner*—Robert T. Bond
*Attorney, Agent, or Firm*—Wegner & Bretschneider

[57] ABSTRACT

This invention relates to 4,5-deoxymaytansinoid compounds represented by the formula

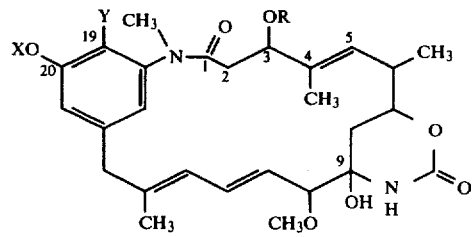

wherein X is a hydrogen atom or an alkyl or acyl group, Y is a hydrogen or chlorine atom, and R is a hydrogen atom or a carboxylic acid-derived acyl group, and methods of producing the same. The compounds are useful as antitumor, antiprotozoal and antifungal agents.

12 Claims, No Drawings

4,5-DEOXYMAYTANSINOIDS, THEIR USE AND PHARMACEUTICAL COMPOSITIONS THEREOF

FIELD OF ART

This invention relates to novel 4,5-deoxymaytansinoid compounds useful, for example, as drugs and methods of producing the same.

BACKGROUND ART

Among a series of compounds similar in skeletal structure to the compounds of the present invention, there are maytansine and related compounds (maytanprine, maytanbutine, maytanvaline, maytanbutacine, etc.) isolated from plants by S. M. Kupchan et al.*, as well as colubrinol and colubrinol acetate obtained by M. C. Wani et al.** All of these are potent and characteristic mitosis inhibitors and have antitumor activity. However, since natural resources contain only trace amounts of these compounds, there have been the problem of supply thereof.
*S. M. Kupchan et al., J. Amer. Chem. Soc., 94, 1354 (1972); S. M. Kupchan et al., J. Chem. Soc., Chem. Comm., 1972, 1605: S. M. Kupchan et al., J. Org. Chem., 42, 2349 (1977).
**M. C. Wani et al., J. Chem. Soc., Chem. Comm., 1973, 390.

Recently, Higashide et al.* have found among the metabolites produced by a microorganism regarded as belonging to the genus Nocardia a group of ansamitocin compounds which have the same skeletal structure as the above-mentioned compounds have but are different therefrom with regard to the ester side chain in position 3, and furthermore they have ascertained that said ansamitocin compounds have excellent antitumor activity at least comparable to that of maytansine.
*E. Higashide et al., Nature, vol. 270, 271 (1977).

DISCLOSURE OF THE INVENTION

The present inventors have succeeded in synthesizing novel 4,5-deoxymaytansinoid compounds which are different in part of the principal skeletal structure from the above-mentioned known maytansinoids, have found that they have excellent biological activities, and have now completed the present invention.

Thus, the present invention is concerned with 4,5-deoxymaytansinoid compounds represented by the formula

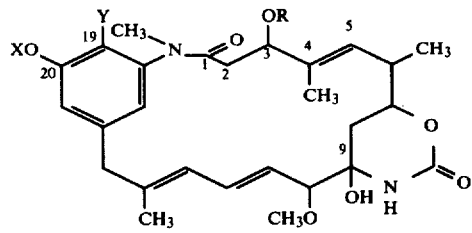

(I)

wherein X is a hydrogen atom or an alkyl or acyl group, Y is a hydrogen or chlorine atom, and R is a hydrogen atom or a carboxylic acid-derived acyl group, as well as methods for production thereof.

In the above formula (I), the carboxylic acid-derived acyl group represented by R includes those acyl groups that are derived from carboxylic acids having molecular weight of about 300 or less, or acyl groups containing about 1–20 carbon atoms. Such acyl groups include among others saturated or unsaturated aliphatic acyl groups, saturated or unsaturated alicyclic acyl groups, aromatic acyl groups and N-acyl-α-amino acid-derived acyl groups, and may be represented, for example, by the formula $$-COR^1 \quad (A)$$

wherein $R^1$ is a hydrogen atom or an alkyl, alkenyl, cycloalkyl, cycloalkenyl or aryl group, which may have a substituent or substituents, and wherein said group, when cyclic, may be bound to the carbonyl group through an alkylene chain. Among them, specific examples of those groups that are substituted are N-acyl-α-aminoacyl groups represented by the formula

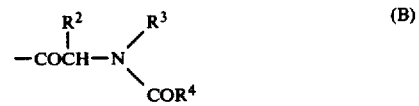

(B)

wherein $R^2$ is a hydrogen atom or an alkyl, cycloalkyl or aryl group, wich may be substituted and, when cyclic, may be bound to the carbon atom in the α-position through an alkylene chain, $R^3$ is a hydrogen atom or an alkyl, cycloalkyl or aryl group, which may be substituted and, when cyclic, may be bound to the N atom through an alkylene chain, and $R^4$ is a hydrogen atom, an alkyl, alkenyl, cycloalkyl, cycloalkenyl or aryl group, which may be substituted and, when cyclic, may be bound to the carbonyl group on the N atom, or an alkoxy or benzyloxy group.

In the following, detailed mention is made of the moiety $R^1$ of the acyl group represented by the above formula (A).

The alkyl group represented by $R^1$ includes among others alkyl groups containing about 1–18 carbon atoms, such as methyl, ethyl, propyl, isopropyl, butyl, isobutyl, sec-butyl, tert-butyl, pentyl, isopentyl, hexyl, heptyl, octyl, nonyl, decyl, undecyl, dodecyl, tridecyl, pentadecyl and heptadecyl. Preferred are alkyl groups of about 1–6 carbon atoms.

The alkenyl group represented by $R^1$ includes among others alkenyl groups containing about 2–10 carbon atoms, such as vinyl, allyl, 1-methylvinyl, 2-methylvinyl, 1-octenyl and 1-decenyl. Preferred are alkenyl groups of about 2–4 carbon atoms.

The cycloalkyl group represented by $R^1$ includes among others cycloalkyl groups containing about 3–10 carbon atoms, such as cyclopropyl, cyclobutyl, cyclopentyl, cyclohexyl, cycloheptyl, cyclooctyl, norbornyl and adamantyl, and the cycloalkenyl group includes among others cycloalkenyl groups containing about 3–10 carbon atoms, such as 1-cyclobutenyl, 1-, 2- or 3-cyclopentenyl, 1-, 2- or 3-cyclohexenyl, 4-cycloheptenyl, 4-cyclooctenyl, 1,4-cyclohexadienyl, 4-norbornenyl and 2,4,6-cycloheptatrienyl.

The aryl group represented by $R^1$ includes among others phenyl and naphthyl, among which phenyl is preferred.

The alkyl, akenyl, cycloalkyl, cycloalkenyl and aryl groups each represented by the above-mentioned $R^1$ may be substituted. The substituent includes among others alkoxy groups of 1–4 carbon atoms (e.g. methoxy, ethoxy, propoxy, isopropoxy, butoxy, isobutoxy, sec-butoxy, tert-butoxy), alkanoyl groups of 2–4 carbon atoms (e.g. acetyl, propionyl, butyryl, isobutyryl), alkanoyloxy groups of 2–4 carbon atoms (e.g. acetyloxy, propionyloxy, butyryloxy, isobutyryloxy), alkoxycarbonyl groups of 2–4 carbon atoms (e.g. methoxycarbonyl, ethoxycarbonyl, propoxycarbonyl, isopropoxycarbonyl), halogen atoms (e.g. chlorine, fluorine, bromine, iodine), hydroxyl, nitro, cyano, trifluoromethyl, amino, mono($C_{1-4}$ alkyl)amino groups (e.g. methylamino), di($C_{1-4}$ alkyl)amino groups (e.g. dimethylamino, diethylamino, dipropylamino, diisopropylamino, dibutylamino), alkylthio groups of 1–4 carbon atoms (e.g. methylthio, ethylthio, propylthio, isopropylthio, butylthio, isobutylthio, sec-butylthio, tert-butylthio), $C_{1-4}$ alkylsulfinyl groups, $C_{1-4}$ alkanesulfonyl groups, oxo, thioxo, $C_{1-4}$ alkanoylamino groups (e.g. formylamino, acetylamino, propionylamino, butyrylamino, isobutyrylamino), and, for the cases where $R^1$ is a cyclic group (cycloalkyl, cycloalkenyl or aryl), alkyl groups of 1–4 carbon atoms (e.g. methyl, ethyl, propyl, isopropyl, butyl, isobutyl, sec-butyl, tert-butyl). The group $R^1$ may have one to three such substituents, which may be the same or different.

When cyclic, the above-mentioned group $R^1$ (optionally substituted cycloalkyl, cycloalkenyl or aryl) may be bound to the carbonyl group of the —$COR^1$ group via an alkylene chain. Such alkylene chain includes straight or branched alkylene chains of about 1–4 carbon atoms, such as methylene, ethylene, methylmethylene (ethylidene), propylene, butylene, 1-, 2- or 3-methylpropylene, 1- or 2-ethylethylene, propylmethylene, 1,1- or 1,2-dimethylethylene and isopropylmethylene. The alkylene chain may also be substituted by one or more of the above-mentioned substituents. Thus, for the cases where the above-mentioned cyclic group is bound to the alkylene chain, $R^1$ represents an optionally substituted cycloalkylalkyl, cycloalkenylalkyl or aralkyl group.

Examples of the substituted $C_{1-18}$ alkyl group represented by $R^1$ are methoxymethyl, butoxymethyl, methylthiomethyl, methylthioethyl, ethylthioethyl, isopropylthioethyl, butylthioethyl, isobutylthioethyl, acetyloxymethyl, acetyloxyethyl, ethoxycarbonylmethyl, butoxycarbonylethyl, fluoromethyl, chloromethyl, chloroethyl, 3-chloropropyl, 4-chlorobutyl, 3,3,3-trichloropropyl, trifluoromethyl, bromomethyl, 4-bromobutyl, 5-bromopentyl, iodomethyl, 2-iodoethyl, 1,1-dimethyl-2,2-dichloroethyl, 2-chloro-1-chloromethyl-1-methylethyl, cyanomethyl, methylsulfinylethyl and methylsulfonylmethyl.

The substituted $C_{2-10}$ alkenyl group represented by $R^1$ is, for example, 2-chlorovinyl.

Examples of the substituted $C_{3-10}$ cycloalkyl group represented by $R^1$ are 2,2-dimethylcyclopropyl, 2-propylcyclopropyl, 2-butylcyclopropyl, 4-isobutylcyclohexyl, 2-bromocyclopropyl, 2-chlorocyclobutyl, 4-chlorocyclohexyl, 2-iodocyclohexyl, 2,2-difluorocyclobutyl, 3-methoxycyclohexyl, 2,2-dimethyl-3-acetylcyclobutyl, 4-acetylcyclohexyl, 2-cyanocyclohexyl, 2-cyanocyclobutyl, 4-cyanocyclohexyl and 4-dimethylaminocyclohexyl.

Examples of the substituted $C_{3-7}$ cycloalkenyl group represented by $R^1$ are 2-cyano-2-cyclohexenyl, 3,3-dimethyl-4-cyclobutenyl, 4-ethoxycarbonyl-1-cyclohexenyl and 4-butoxycarbonyl-1-cyclohexenyl.

Examples of the substituted aryl group represented by $R^1$ are 2-, 3- or 4-methylphenyl, 4-tert-butylphenyl, 2-, 3- or 4-chlorophenyl, 2-, 3- or 4-bromophenyl, 2-, 3- or 4-iodophenyl, 2-, 3- or 4-fluorophenyl, 2- or 4-methoxyphenyl, 4-butoxyphenyl, 4-methoxycarbonylphenyl, 3-acetylphenyl, 2-, 3- or 4-nitrophenyl, 3- or 4-cyanophenyl, 4-dimethylaminophenyl, 4-diethylaminophenyl, 4-acetoxyphenyl, 4-butyryloxyphenyl, 2,4-, 2,5-, 2,6-, 3,4- or 3,5-dichlorophenyl, 3,4-dimethoxyphenyl, 3,4,5-trimethoxyphenyl, 3,4-methylenedioxyphenyl, 3-trifluoromethylphenyl, 4-methylthiophenyl, 4-methylsulfonylphenyl and 4-acetamidophenyl.

When the cyclic group [e.g. cycloalkyl, aryl (especially phenyl)], detailedly mentioned in the above with reference to $R^1$, is bound to the carbonyl carbon of the acyl group of formula (A) via an alkylene chain, $R^1$ substantially represents a group composed of such cyclic group and an alkylene chain bound thereto, such as a cycloalkylalkyl or aralkyl group. Examples of such cycloalkylalkyl group are adamantylmethyl, cyclohexylmethyl, 3-cyclohexylpropyl, 2-cyclopentenylmethyl and 2-cyclopentylethyl, and examples of such aralkyl group are 4-bromobenzyl, 2-, 3- or 4-chlorobenzyl, 2,5- or 3,4-dimethoxybenzyl, 4-ethoxybenzyl, 4-fluorobenzyl, 3- or 4-methoxybenzyl, 4-methoxyphenylethyl, 1- or 2-naphthylmethyl, 2-, 3- or 4-nitrobenzyl, 3-nitrophenethyl, benzyl, 2-, 3- or 4-phenylpropyl, 2-, 3- or 4-methylbenzyl, 3,4,5-trimethoxybenzyl and α-methylphenethyl.

The N-acyl-α-aminoacyl group represented by the above formula (B) is described hereinafter.

The alkyl, alkenyl, cycloalkyl, cycloalkenyl are aryl groups defined with regard to $R^2$, $R^3$ and/or $R^4$ are illustrated by the respective examples given with reference to the above-mentioned group $R^1$. These groups may be substituted, and the substituents are as those given as examples of the substituents on the above-mentioned group $R^1$. When $R^2$, $R^3$ and/or $R^4$ is a cyclic group (i.e. cycloalkyl, cycloakenyl or aryl), the cyclic group may be bound to the carbon atom in the α-position, to the N atom or to the carbonyl group on the N atom of the group of formula (B) via an alkylene chain, which may be illustrated by the examples given with reference to the above-mentioned group $R^1$.

The alkoxy group represented by $R^4$ includes among others alkoxy groups of about 1–4 carbon atoms, such as methoxy, ethoxy, propoxy, isopropoxy, butoxy, isobutoxy, sec-butoxy and tert-butoxy.

Typical examples of the N-acyl-α-aminoacyl group represented by formula (B) are N-acetyl-N-methylglycyl, N-benzoyl-N-methylglycyl, N-(4-chlorobenzoyl)-N-methylglycyl, N-acetyl-N-methylalanyl, N-acetyl-N-benzylalanyl, N-acetyl-N-methylleucyl, N-isobutyryl-N-methylalanyl, N-isovaleryl-N-methylalanyl, N-propionyl-N-methylalanyl, N-acetyl-N-methylphenylalanyl, 2-(N-acetyl-N-methyl)amino-3-methoxycarbonylpropionyl, 2-(N-acetyl-N-methyl)amino-3-methylmercaptopropionyl, 2-(N-acetyl-N-methyl)amino-3-ethylmercaptopropionyl, N-acetyl-N-methylisoleucyl, N-acetyl-N-methylleucyl, N-acetyl-N-methylmethionyl, N-acetyl-N-methyl-4'-acetoxytyrosinyl, N-benzyl-N-methylvalyl, N-acetyl-N-methylphenylglycyl, N-acetyl-N-methyl-3-cyanoalanyl and N-acetyl-N-methyl-(4'-dimethylamino)phenylalanyl.

Referring to the above formula (I), the acyl group represented by X includes the same carboxylic acid-derived acyl groups as those mentioned above with reference to R, and further organic sulfonic acid-derived acyl groups represented by the formula $$—SO_2R^5 \qquad (C)$$

wherein $R^5$ is an optionally substituted alkyl or aralkyl group, and carbamic acid-derived acyl groups represented by the formula

—CONR$^6$R$^7$ (D)

wherein R$^6$ and R$^7$ are the same or different and each is a hydrogen atom or an optionally substituted alkyl, cycloalkyl, aralkyl or aryl group.

The alkyl group represented by R$^5$ includes alkyl groups of about 1–4 carbon atoms, such as methyl, ethyl, propyl, isopropyl, butyl, isobutyl, sec-butyl and tert-butyl, and aralkyl groups of about 7–9 carbon atoms, such as benzyl, phenethyl and α-methylbenzyl.

When the above R$^5$ is an aralkyl group, said group may have at least one substituent, and the substituent includes among others C$_{1-4}$ alkyl (e.g. methyl, ethyl, propyl, isopropyl butyl, isobutyl, sec-butyl, tert-butyl), C$_{1-4}$ alkoxy (e.g. methoxy, ethoxy, propoxy, isopropoxy, butoxy), nitro, amino, mono- or di(C$_{1-4}$ alkyl)amino (e.g. methylamino, ethylamino, dimethylamino, diethylamino), mono- or di(C$_{1-4}$ alkanoyl)amino (e.g. formylamino, acetylamino, propionylamino, butyrylamino), halogen-substituted mono- or di(C$_{1-4}$ alkanoyl)amino (e.g. trifluoroacetylamino, chloroacetylamino, dichloroacetylamino), halogen (e.g. fluorine, chlorine, bromine, iodine) and haloalkyl (e.g. trifluoromethyl).

Referring to the above R$^5$, preferred examples of the group R$^5$SO$_2$— are methanesulfonyl, ethanesulfonyl, 2-propanesulfonyl, 2-butanesulfonyl, butanesulfonyl, α-toluenesulfonyl (benzylsulfonyl), β-ethylbenzenesulfonyl, α-phenylpropanesulfonyl, benzenesulfonyl, p-toluenesulfonyl, p-chlorobenzenesulfonyl, o-, m- or p-nitrobenzenesulfonyl, p-methoxybenzenesulfonyl, p-acetamidobenzenesulfonyl, p-trifluoroacetamidobenzenesulfonyl, p-aminobenzenesulfonyl, p-methylaminobenzenesulfonyl and p-dimethylaminobenzenesulfonyl.

Referring to the above R$^6$ and R$^7$, the alkyl group represented either of them includes among others C$_{1-6}$ alkyl groups (e.g. pentyl and hexyl as well as those groups mentioned as examples of R$^5$), the cycloalkyl group includes C$_{3-6}$ cycloalkyl groups, namely cyclopropyl, cyclobutyl, cyclopentyl and cyclohexyl, and the aralkyl group includes benzyl and phenethyl, and the aryl group includes phenyl, α- and β-naphthyl.

The alkyl, cycloalkyl, aralkyl and aryl groups represented by either of the above R$^6$ and R$^7$ may have at least one substituent, and the substituent includes those substituents mentioned above as examples of the substituent on the aralkyl group represented by R$^5$.

Referring to the above R$^6$ and R$^7$, preferred examples of the group R$^6$R$^7$NCO— are N-methylcarbamoyl, N-isopropylcarbamoyl, N-butylcarbamoyl, N-hexylcarbamoyl, N-cyclohexylcarbamoyl, N-benzylcarbamoyl, N-phenylcarbamoyl, N-2-methoxyethylcarbamoyl, N-p-chlorophenylcarbamoyl, N-p-methoxyphenylcarbamoyl and N,N-dimethylcarbamoyl.

Referring to the above-mentioned formula (I), the alkyl group represented by X includes among others alkyl groups of 1–8 carbon atoms, such as methyl, ethyl, propyl, isopropyl, butyl, sec-butyl, pentyl, isopentyl, hexyl, heptyl and octyl. These alkyl groups represented by X may have at least one substituent, and the substituent includes among others halogen atoms (e.g. chlorine, bromine, iodine), carboxyl, C$_{2-5}$ alkoxycarbonyl groups (e.g. methoxycarbonyl, ethoxycarbonyl, isopropoxycarbonyl, butoxycarbonyl, tert-butoxycarbonyl), phenoxycarbonyl, benzyloxycarbonyl, hydroxyl, C$_{1-4}$ alkoxy groups (e.g. methoxy, ethoxy, propoxy, isopropoxy, butoxy, isobutoxy, sec-butoxy, tert-butoxy; these may be substituted on the terminal carbon by a C$_{1-4}$ alkoxy group or —O—(CH$_2$CH$_2$O)$_n$—H where n is an integer of 1–5), benzyloxy, C$_{1-4}$ alkylthio groups (e.g. methylthio, ethylthio, propylthio, butylthio), benzylthio, phenylthio, C$_{1-4}$ alkylsulfinyl groups (e.g. methylsulfinyl, ethyl-sulfinyl, propylsulfinyl, butylsulfinyl), benzylsulfinyl, phenylsulfinyl, C$_{1-4}$ alkylsulfonyl groups (e.g. methylsulfonyl, ethylsulfonyl, propylsulfonyl, butylsulfonyl), benzylsulfonyl, phenylsulfonyl, alkanoyloxy groups (e.g. formyloxy, acetyloxy, propionyloxy, butyryloxy, isobutyryloxy, valeryloxy, pivaloyloxy), benzoyloxy, phenylacetyloxy, cyano, dialkylamino groups (e.g. dimethylamino, diethylamino, dibutylamino), one or two oxo groups which may be acetalized with lower (C$_{1-4}$) alcohol, diol, mercaptan or dimercaptol or converted to an imino group with hydrazine or a substituted hydrazine, lower (C$_{1-4}$) 1-alkylidene (e.g. methylene, ethylidene, propylidene) which may be substituted e.g. by lower (C$_{1-4}$) alkoxycarbonyl or cyano, phenyl, α- or β-naphthyl, vinyl, ethynyl, C$_{3-6}$ cycloalkyl groups (e.g. cyclopropyl, cyclobutyl, cyclopentyl, cyclohexyl), 5- or 6-membered N-, O- and/or S-containing heterocyclic groups (e.g. pyridyl, pyrimidyl, pyrazinyl, pyridazinyl, triazinyl, piperidinyl, piperazinyl, pyrrolyl, pyrrolidinyl, pyrrolinyl, imidazolyl, pyrazolyl, triazolyl, tetrazolyl, imidazolinyl, pyrazolidinyl, imidazolidinyl, triazolidinyl, furyl, furanyl, tetrahydrofuryl, thienyl, morpholino, oxazolyl, oxazolinyl, thiazolyl, thiazolinyl, oxadiazolyl, thiadiazolyl), oxiranyl, dioxolanyl and dithiolanyl.

Among the above-mentioned groups, the cyclic groups as well as vinyl and ethynyl may be further substituted, and the substituent includes among others C$_{1-4}$ alkyl groups (e.g. methyl, ethyl, propyl, isopropyl, butyl, isobutyl, sec-butyl, tert-butyl), hydroxyl, C$_{1-4}$ alkoxy groups (e.g. methoxy, ethoxy, propoxy, isopropoxy, butoxy, isobutoxy, sec-butoxy, tert-butoxy), C$_{1-4}$ alkanoyloxy groups (e.g. formyloxy, acetyloxy, propionyloxy, butyryloxy, isobutyryloxy), C$_{2-5}$ alkoxycarbonyl groups (e.g. methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl), halogen atoms (e.g. chlorine, fluorine, bromine, iodine), nitro, cyano, trifluoromethyl, amino, mono(C$_{1-4}$alkyl)amino groups (e.g. methylamino, ethylamino, propylamino, isopropylamino, butylamino, isobutylamino), di(C$_{1-4}$alkyl)amino groups (e.g. dimethylamino, diethylamino, dipropylamino, dibutylamino), C$_{1-4}$ alkylthio groups (e.g. methylthio, ethylthio, propylthio, isopropylthio, butylthio, isobutylthio, sec-butylthio, tert-butylthio), C$_{1-4}$ alkylsulfinyl groups (e.g. methylsulfinyl), C$_{1-4}$ alkanesulfonyl groups (e.g. methanesulfonyl), C$_{1-4}$ alkanoylamino groups (e.g. formylamino, acetylamino, propionylamino, butyrylamino, isobutyrylamino), sulfo, sulfamoyl groups (e.g. sulfamoyl, N-methylsulfamoyl, N,N-dimethylsulfamoyl), sulfonylamino groups (e.g. methanesulfonylamino, benzenesulfonylamino, p-toluenesulfonylamino), C$_{2-4}$ alkanoyl groups (e.g. acetyl, propionyl, butyryl, isobutyryl), benzyloxy, benzylthio, benzyloxycarbonyloxy, tert-butoxycarbonyloxy and benzylamino.

Typical examples of the compounds (I) of the present invention include 4,5-deoxymaytansinol, 19-dechloro-4,5-deoxymaytansinol, 20-demethoxy-20-hydroxy-4,5-deoxymaytansinol, 4,5-deoxyansamitocin P-3 (4,5-deoxymaytansinol 3-isobutyrate), 4,5-deoxymaytansine, 4,5-deoxymaytansinol 3-phenylacetate, 4,5-deoxymaytansinol, 3-crotonate, 4,5-deoxymaytansinol 3-cyclobutanecarboxylate, 4,5-deoxymaytansinol 3-phenoxyacetate, 4,5-deoxymaytansinol 3-mandelate, 4,5-deoxymaytansinol, 3-α-aminophenylacetate, 4,5-deoxymaytansinol, 3-α-chlorophenylacetate, 20-demethoxy-20-hydroxy-4,5-deoxymaytansinol-3-isobutyrate (4,5-deoxy-PDM-3), 20-demethoxy-20-phenacyloxy-4,5-deoxymaytansine, 20-demethoxy-20-(3-ethoxycarbonyl)acetonyloxy-4,5-deoxymaytansinol 3-isobutyrate (4,5-deoxy-PDM-3-C$_{20}$-(3-ethoxycarbonyl)acetonyl ether), 4,5-deoxy-PDM-3-C$_{20}$-hexaethylene glycolyl ether, 4,5-deoxy-PDM-3-C$_{20}$-p-aminobenzyl ether, 4,5-deoxy-PDM-3-C$_{20}$-allyl ether, 4,5-deoxy-PDM-3-C$_{20}$-β-cyanovinyl ether, 4,5-deoxy-PDM-3-C$_{20}$-crotonate, 4,5-deoxy-PDM-3-C$_{20}$-benzoate, 4,5-deoxy-PDM-3-C$_{20}$-cyclohexanecarboxylate, 4,5-deoxy-PDM-3-C$_{20}$—N-phenylcarbamate, 4,5-deoxy-PDM-3-C$_{20}$-methanesulfonate, 19-dechloro-4,5-deoxy-ansamitocin P-3 and 19-dechloro-4,5-deoxymaytansinol 3-[2-(N-acetyl-N-methyl)]amino-4-methylpentanoate.

The 4,5-deoxymaytansinoid compounds (I) of the present invention can be produced, for example, by the following methods:

(1) Deoxygenating a compound of the formula

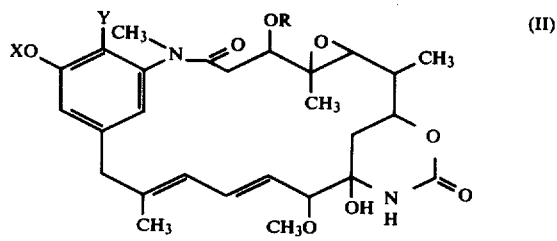

wherein the symbols are as defined above;

(2) reacting a 4,5-deoxymaytansinoid compound of the formula

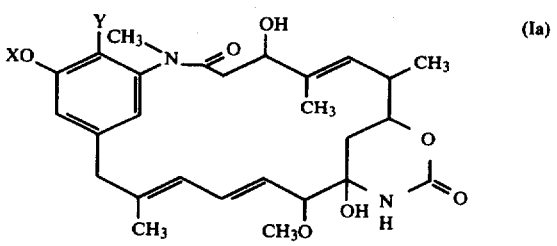

wherein the symbols are as defined above, with a carboxylic acid of the formula

wherein R$^8$ is acyl derived from C$_{1-20}$ carboxylic acid, or a reactive derivative thereof; and (3) alkylating or acylating a 4,5-deoxymaytansinoid compound of the formula

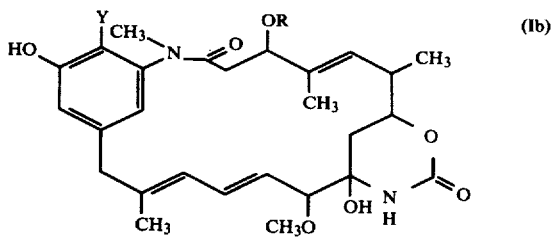

wherein the symbols are as defined above.

During each of the above-mentioned reactions, the hydroxyl group in position 9 of the starting material may, if necessary, be protected by an adequate protective group (e.g. C$_{1-4}$ alkyl, tri-C$_{1-4}$-alkylsilyl, 2-tetrahydropyranyl). Said protective group can easily be removed after the reaction by treatment with an aqueous medium (e.g. hydrous methanol, hydrous ethanol, hydrous tetrahydrofuran, hydrous acetonitrile, hydrous acetic acid) or an acid (e.g. inorganic acid such as hydrochloric acid, sulfuric acid or phosphoric acid; an organic acid such as trifluoroacetic acid, trichloroacetic acid, methanesulfonic acid or p-toluenesulfonic acid).

The deoxygenation reaction in Method (1) mentioned above is carried out in the presence of a metal or a halide of a low valent metal. Preferred metals are titanium and zinc-copper complex, and preferred low valent metal halides are chromous halides (e.g. chromous chloride), lanthanous halides (e.g. samarium dibromide, ytterbium dibromide), low valent tungsten halides (e.g. prepared from tungsten hexachloride/butyllithium), low valent titanium halides (e.g. titanium trichloride/lithium aluminum hydride) and low valent iron halides (e.g. ferric chloride/butyllithium). They are usually used in an amount of about 1-100 moles, preferably about 5-50 moles, per mole of starting material (II). The reaction is preferably carried out in the presence of a solvent, and the solvent includes among others ethers (e.g. diethyl ether, tetrahydrofuran), among which tetrahydrofuran is especially preferable. The reaction can usually be carried out at about −70° C. to +150° C., preferably at about −40° C. to +80° C. After completion of the reaction, the excess reagent is decomposed with water or an alcohol (e.g. methanol, ethanol), and then the product is extracted with an adequate solvent (e.g. ethyl acetate, chloroform). The crude product thus obtained can be purified by silica gel column chromatography or high performance liquid chromatography to give the desired 4,5-deoxymaytansinoid compound (I).

The acylation of compound (Ia) in Method (2) or of compound (Ib) in Method (3) is carried out, in accordance with the known methods of acylating maytansinols and 20-demethoxy-20-hydroxymaytansinoids, by reacting (Ia) or (Ib) with carboxylic acid (III) in the presence of a carbodiimide (e.g. dicyclohexylcarbodiimide) or by reacting (Ia) or (Ib) with a reactive derivative (e.g. acid anhydride) of (III) or a reactive derivative of other acid (e.g. sulfonic acid chloride, carbamic acid chloride, isocyanate) [see e.g. U.S. Pat. No. 4,256,746, European Patent Publication No. 14,402 and U.S. Pat. No. 4,264,596].

In cases where carboxylic acid (III) or other acid derivative to be used in the above acylation reaction has a substituent susceptible to said reaction (e.g. amino, hydroxyl group), such substituent can be protected by an adequate protective group (e.g. benzyloxycarbonyl, tert-butyloxycarbonyl, etc. for amino protection; benzyloxycarbonyl, acetyl, trifluoroacetyl, etc. for hydroxyl protection) prior to the reaction. In such cases, the desired compound (I) can be obtained by removing said protective group by a conventional method after the reaction.

When X in compound (Ia) is a hydrogen atom (i.e. when a hydroxyl group is present in position 20), not only the hydroxyl group in position 3 but also the hydroxyl group in position 20 can be simultaneously acylated by the above-mentioned acylation and as a result compound (I) wherein X is an acyl group is produced. In this case, if necessary, the compound wherein X is an acyl group may be subjected to aminolysis or to alkaline hydrolysis for selective removal of the acyl group in position 20, to give (I) wherein X is a hydrogen atom. The aminolysis is carried out by treating compound (I) with an amine (e.g. ethylenediamine phenylenediamine, hydrazine, guanidine, diethylamine) in a solvent (e.g. dichloromethane, chloroform, tetrahydrofuran). The alkaline hydrolysis is carried out in a hydrous solvent (e.g. hydrous methanol, hydrous ethanol, hydrous tetrahydrofuran) or a mixture of such a hydrous solvent and an organic solvent (e.g. diethyl ether, dichloromethane, chloroform, benzene, toluene) with an alkali metal hydroxide (e.g. potassium hydroxide, sodium hydroxide) or an alkali metal carbonate (e.g. potassium carbonate, sodium carbonate), for instance.

The alkylation of compound (Ib) in Method (3) is carried out, in accordance with the known method of alkylating the hydroxyl group in position 20 of 20-demethoxy-20-hydroxy-maytansinoids [European Patent Publication No. 25,496], by reacting compound (Ib), in an adequate solvent, e.g. lower alkanonol (methanol, ethanol), generally in the presence of a base, with (a) a diazoalkane (e.g. diazomethane, α-diazotoluene, (b) a trialkyloxonium salt (e.g. trimethyloxonium fluoroborate, triethyloxonium fluoroborate), (c) a halide (e.g. butyl bromide, benzyl bromide, allyl chloride, propargyl bromide, 1-bromoacetone, α-bromoacetophenone, ethyl bromoacetate, ethyl 4-chloroacetoacetate, bromoacetaldehyde diethyl acetal), (d) a sulfate (e.g. dimethyl sulfate, carbitol p-toluenesulfonate), (e) an isourea (e.g. O-methyl-N,N'-dicyclohexylisourea), (f) a quaternary ammonium salt (e.g. 1-benzylpyridinium-p-toluenesulfonate) or (g) an acetylene (e.g. diethyl acetylenedicarboxylate, cyanoacetylene), for instance. Usable bases include alkali metal hydroxides (e.g. sodium hydroxide), tertiary amines (e.g. triethylamine, pyridine, 4-dimethylaminopyridine, N-methylmorpholine), etc. In some cases, the reaction is preferably carried out in a two-phase system consisting of an alkaline aqueous layer and an organic layer in the presence of a so-called phase transfer catalyst (e.g. tetraethylammonium bromide, cetyltrimethylammonium bromide). In case the alkyl group to be introduced has a group susceptible to alkylation, the objective compound can be obtained, as in the case of Method (2) mentioned above, by first producing a corresponding compound wherein the susceptible group is protected and then removing the protective group. Furthermore, it is possible, by using known methods, to react a product compound wherein an oxo group is contained within said alkyl group with a hydrazine or hydroxylamine so as to produce a corresponding hydrazone or oxime; to oxidize a product compound wherein a thio ether group is contained within said alkyl group with an adequate oxidizing agent (e.g. hydrogen peroxide, m-chloroperbenzoic acid), for instance, so as to produce a corresponding compound containing a sulfinyl or sulfonyl group; to reduce a product compound wherein a nitro group is contained within said alkyl group by a conventional method (e.g. with zinc powder and calcium chloride) so as to produce a corresponding amino-group-containing compound; or to acylate the amino group of the thus-produced amino-containing alkyl group so as to convert said amino group to an acyl-amino group.

The 4,5-deoxymaytansinoid compounds (I) produced by the above-mentioned methods can be isolated from the reaction mixture by a conventional technique adequately chosen, such as, for example, concentration, solvent extraction, chromatography and/or recrystallization. In case the objective compound is produced as a mixture of isomers (e.g. D-isomer and L-isomer), the respective isomers can generally be separated from each other by a known method of separation, silica gel column chromatography, for instance. Therefore, it should be noted that the 4,5-deoxymaytansinoid compounds (I) of the present invention include individual isomers thereof as well as isomeric mixtures thereof.

The 4,5-deoxymaytansinoid compounds (I), of the present invention have potent mitosis-inhibiting and antitumor activities and relatively low toxicity, and, when administered to animals suffering from malignant tumors [e.g. leukemia (P-388, mouse), melanoma (B-16, mouse)], produce significant life span prolonging effect, and therefore can be used as effective antitumor agents for warm-blooded animals. The compounds (I) are usually administered safely either orally or parenterally in the form of adequate pharmaceutical compositions (e.g. injections) with known carriers, diluents and so on. When the compounds (I) are administered by injection, it can be done adequately, for example, subcutaneously, intraperitonealy, intravenously or intramuscularly, and, for intravenous injection in treating melanoma, for instance, the dose can adequately be determined with due consideration for the symptom, animal species to be treated, and so on, within the range of about 1–1,000, preferably 5–500, μg/kg body weight/injection.

An injectable solution may be prepared, for example, by dissolving compound (I) in an amount of about 50 μg to about 3 mg in an alcohol (e.g. ethanol) in an amount of about 0.5 ml and adding physiological saline in an amount sufficient to make the total volume 10 ml. When the dose is small, this solution may further be diluted with physiological saline.

The compounds (I) of the present invention are also useful in that they exhibit antimicrobial activity, for example, antifungal or antiprotozoal activity. Thus, for example, the compounds (I) can advantageously be used as antifungal or antiprotozoal agents in studying the bacterial flora in soil, activated sludge or animal body fluids. Thus, in isolating useful bacteria from soil or in checking the activity of bacteria alone, namely microbes other than protozoa and fungi, for operation and analysis of the activated sludge process of waste water treatment, the use of the compounds can allow selective growth of the bacterial flora without allowing growth of fungi or protozoa present in samples. More detailedly, a test sample is added to a liquid or solid culture medium, then an about 10–100 μg/ml solution of compound (I) in water containing 1% of methanol is added in an amount of 0.1 ml per ml of the medium, and incubation is conducted.

Furthermore, the compounds (I), at a dose of 0.02 ml of 1 mg/ml aqueous solution, can inhibit growth of phytopathogenic microorganisms capable of causing stem rot, Helminthosporium leaf spot and sheath blight of the rice plant, and therefore can be used in the treatment of such plant diseases by spraying the rice plant with a solution prepared by dissolving compound (I) in 1% aqueous methanol in a concentration of about 0.5–5 μg/ml.

As the starting compounds (II) to be used in producing the compounds of the present invention, there may be used known maytansines and ansamitocins as they are, as well as maytansinol, dechloromaytansinoid [U.S. Pat. No. 4,256,746] and 20-demethoxy-20-hydroxymaytansinoid [European Pat. Publication No. 4,466], for instance, either as they are or after acylation in position 3 or alkylation in position 20 thereof by known methods.

The starting compound (III) to be used in producing the compounds of the present invention may generally be known carboxylic acids or carboxylic acids prepared by the methods of producing said known ones. The following are some of the papers which describe the known methods of producing the carboxylic acids:
J. R. Coggins and N. L. Benoiton, Can. J. Chem., 49, 1968 (1971);
P. Quitt, J. Hellerback and K. Vogler, Helv. Chim. Acta, 46, 327 (1963);
S. L. Portnova et al., Zh, Obshch. Khim., 38, 428 (1968).

The present invention will be more detailedly illustrated by the following examples, which however, are by no means limitative of the present invention.

EXAMPLE 1

Production of 4,5-deoxymaytansinol

To 6 ml of dried tetrahydrofuran (THF) is added 321 mg of anhydrous titanium trichloride, and the mixture is stirred at room temperature in dry nitrogen atmosphere for 15 minutes while adding thereto portionwise 20 mg of lithium aluminum hydride (LAH). Thereafter, 50 mg of maytansinol is added, and the mixture is stirred at room temperature for about 30 minutes. Then, 15 ml of water is added, and the reaction mixture is extracted with chloroform, and the organic layer is washed with water and dried over anhydrous sodium sulfate. The chloroform is distilled off under reduced pressure, and the residue is purified by silica gel column chromatography [silica gel (Merck) Art 7736; solvent system: chloroform:methanol=100:1.5] to give 22 mg of 4,5-deoxymaytansinol. Yield=45.1%. Mass spectrum (m/e): 548 (M+), 530, 487.

EXAMPLE 2

Production of 4,5-deoxydechloromaytansinol

To 60 ml of dried THF is added 4.7 g of anhydrous titanium trichloride, and the mixture is stirred at room temperature in a dry nitrogen atmosphere for 15 minutes while adding thereto portionwise 300 mg of LAH. Thereafter, 500 mg of dechloromaytansinol is added, and the mixture is stirred at room temperature for about 40 minutes. The reaction mixture is treated in a manner similar to that in Example 1. Purification of the crude product by silica gel column chromatography [silica gel (Merck); chloroform:methanol=100:1.5] gives 200 mg of 4,5-deoxydechloromaytansinol. Yield=41.3%. Mass spectrum (m/e): 514 (M+), 496, 453.

EXAMPLE 3

Production of 4,5-deoxy-20-demethoxy-20-hydroxymaytansinol

To 6 ml of dried THF is added 321 mg of anhydrous titanium trichloride, and the mixture is stirred at room temperature in a dry nitrogen atmosphere for 15 minutes while adding thereto portionwise 20 mg of LAH. Then, 45 mg of 20-demethoxy-20-hydroxymaytansinol is added, and the mixture is stirred at room temperature for about 40 minutes. The reaction mixture is treated in the same manner as in Example 1. Purification by silica gel column chromatography [silica gel (Merck); chloroform:methanol=50.1] give 12 mg of the title compound. Yield=27.5%. Mass spectrum (m/e): 534 (M+), 516, 473.

EXAMPLE 4

Production of 4,5-deoxyansamitocin P-3 (4,5-deoxymaytansinol 3-isobutyrate)

To 15 ml of dried dichloromethane, there are added 200 mg of 4,5-deoxymaytansinol, 451 mg of N,N'-dicyclohexylcarbodiimide (DCC), 193 mg of isobutyric acid and 97.2 mg of p-dimethylaminopyridine (DMAP), and the mixture is stirred at room temperature. After completion of the reaction, N,N'-dicyclohexylurea is removed from the reaction mixture by filtration, and the filtrate is concentrated under reduced pressure. The residue is dissolved in ethyl acetate, the solution is washed in sequence with 0.1-N hydrochloric acid, saturated aqueous solution of sodium hydrogen carbonate and saturated aqueous solution of sodium chloride, and dried over anhydrous sodium sulfate. The solvent is then distilled off under reduced pressure, and the residue is purified by silica gel column chromatography [silica gel (Merck); chloroform:methanol=100:1.5] to give 70 mg of 4,5-deoxyansamitocin P-3. Yield=31%. Mass spectrum (m/e): 618 (M+), 557.

EXAMPLE 5

Production of 4,5-deoxydechloromaytansine

To 15 ml of dried dichloromethane, there are added 100 mg of 4,5-deoxydechloromaytansinol, 220 mg of DCC, 90 mg of DMAP and 230 mg of N-acetyl-N-methylalanine, and the mixture is stirred at room temperature. After completion of the reaction, the reaction mixture is treated in the same manner as in Example 4. Purification by silica gel column chromatography [silica gel (Merck); chloroform:methanol=100:1] gives two diastereoisomers. Thus 19 mg of 4,5-deoxydechloromaytansine and 10 mg of an isomer thereto having a different configuration within the amino acid side chain are obtained. Mass spectrum (m/e); 641 (M+), 580.

EXAMPLE 6

Production of 4,5-deoxy-20-demethoxy-20-hydroxymaytansinol 3-phenylacetate

To 5 ml of dried dichloromethane, there are added 10 mg of 4,5-deoxy-20-demethoxy-20-hydroxymaytansinol, 22 mg of DCC, 9 mg of DMAP and 30 mg of phenylacetic acid, and the mixture is stirred at room temperature. After completion of the reaction, the reaction mixture is treated in the same manner as in Example 4. Purification by silica gel column chromatography [silica gel (Merck): chloroform:methanol=50:1] gives 5.2 mg of 4,5-deoxy-20-demethoxy-20-hydroxymaytansinol 3-phenylacetate. Mass spectrum (m/e): 652 (M+), 591.

EXAMPLE 7

Production of 4,5-deoxyansamitocin P-3

To 6 ml of dried THF is added 350 mg of anhydrous titanium trichloride, and the mixture is stirred at room temperature for 15 minutes while adding thereto portionwise 22 mg of LAH. Thereafter, 50 mg of ansamitocin P-3 (maytansinol 3-isobutyrate) is added, and the mixture is stirred at room temperature for about 6 hours. After the reaction, 15 ml of water is added, and the mixture is extracted with chloroform. The organic layer is washed with water and dried over anhydrous sodium sulfate. The chloroform is then distilled off under reduced pressure, and the residue is purified by silica gel column chromatography [silica gel (Merck); chloroform:methanol=100:1] to give 5.3 mg of 4,5-deoxyansamitocin P-3. Analysis of this product gives the results which agree with those for the product of Example 4.

EXAMPLE 8

Production of 4,5-deoxymaytansine

To 3 ml of dried dichloromethane, there are added 20 mg of 4,5-deoxymaytansinol, 45 mg of DCC, 32 mg of N-acetyl-N-methyl-DL-alanine and 10 mg of DMAP, and the mixture is stirred at room temperature. After completion of the reaction, the reaction mixture is treated in the same manner as in Example 4. Purification by silica gel column chromatography [silica gel (Merck); ethyl acetate: water-saturated ethyl acetate=3:1] gives two diastereoisomers. Thus 6 mg of 4,5-deoxymaytansine and 7 mg of an isomer thereto having a different configuration within the amino acid side chain are obtained. Mass spectrum (m/e): 675 (M+), 614.

EXAMPLE 9

Production of 20-demethoxy-20-phenacyloxy-4,5-deoxymaytansinol

A mixture of 60 mg of 20-demethoxy-20-hydroxy-4,5-deoxymaytansinol, 107 mg of phenacyl bromide and 35 mg of cetyltrimethylammonium chloride in 2.2 ml of dichloromethane, 2.2 ml of water and 0.3 ml of N NaOH solution is stirred vigorously at room temperature for about 30 minutes. Chloroform is added to the reaction mixture and the organic layer is separated. The aqueous layer is extracted with chloroform. The extracts are combined, washed with a saturated solution of NaHCO₃ and dried. The solvent is removed under reduced pressure and the residue chromatographed on silica gel (20 g) with chloroform/methanol=100/1.5 (v/v). The adequate fractions are combined and the solvent is removed giving 38 mg of 20-demethoxy-20-phenacyloxy-4,5-deoxymaytansinol. Mass spectrum (m/e): 591 (M+-61), 576.

EXAMPLE 10

Production of 20-demethoxy-20-phenacyloxy-4,5-deoxymaytansinol 3-isobutylate.

A solution of 30 mg of 20-demethoxy-20-phenacyloxy-4,5-deoxymaytansinol, 24.3 mg of isobutyric acid, 56.8 mg of DCC and 12.8 mg of DMAP in 4 ml of dry dichloromethane is stirred at room temperature for 9 hours. The reaction mixture is concentrated under reduced pressure and the residue is triturated with ethyl acetate. To this, 0.1 N HCl is added. Insolubles are filtered off and the organic layer is separated from the filtrate. The organic phase is washed with aqueous NaHCO₃ solution and aqueous NaCl solution and dried. The solvent is removed under reduced pressure and the residue chromatographed on silica gel giving 14 mg of 20-demethoxy-20-phenacyloxy-4,5-deoxymaytansinol 3-isobutyrate. Mass spectrum (m/e): 722 (M+), 661 (M+-61), 613.

EXAMPLE 11

Production of 20-demethoxy-20-hydroxy-4,5-deoxymaytansinol 3-isobutyrate

A mixture of 27 mg of 20-demethoxy-20-hydroxy-4,5-deoxymaytansinol, 52.8 mg of isobutyric acid, 155 mg of DCC and 25 mg of DMAP is stirred in 5 ml of dry dichloromethane at room temperature overnight. The reaction mixture is worked up in a manner similar to that in Example 10. The crude product thus obtained is redissolved in 3 ml of dichloromethane. To this, 200 μl of ethylenediamine is added and the mixture is stirred at room temperature overnight. The reaction mixture is diluted with chloroform, washed with 0.1 NHCl, aqueous NaCl solution and dried. The solvent is removed under reduced pressure and the residue chromatographed on silica gel giving 17 mg of 20-demethoxy-20-hydroxy-4,5-deoxymaytansinol 3-isobutyrate. Mass spectrum (m/e): 543 (M+-61), 455.

EXAMPLE 12

Production of 20-demethoxy-20-crotonoyloxy-4,5-deoxymaytansinol 3-isobutyrate

A mixture of 15 mg of 20-demethoxy-20-hydroxy-4,5-deoxymaytansinol 3-isobutylate and 8 mg of crotonic anhydride in 1 ml of pyridine is stirred at room temperature overnight. The reaction mixture is dissolved in 50 ml of ethyl acetate, the solution is washed with 0.5 N HCl, water and aqueous NaCl solution, successively and then dried. Evaporation of the solvent and chromatography of the residual material give 11 mg of 20-demethoxy-20-crotonoyloxy-4,5-deoxymaytansinol 3-isobutyrate. Mass spectrum (m/e): 610, 543, 508.

EXAMPLE 13

Production of 20-demethoxy-20-methylsulfonyloxy-4,5-deoxymaytansinol 3-isobutyrate A mixture of 15 mg of 20-demethoxy-20-hydroxy-4,5-deoxymaytansinol 3-isobutyrate and 12 μl of methanesulfonyl chloride in 1 ml of pyridine is stirred at room temperature overnight. The reaction mixture is worked up in a manner similar to that in Example 12 giving a residue. Chromatography of the residue separated 12.5 mg of 20-demethoxy-20-methylsulfonyloxy-4,5-deoxymaytansinol 3-isobutyrate. Mass spectrum (m/e): 682 (M+), 621 (M+-61).

EXAMPLE 14

Production of 20-demethoxy-20-phenylcarbomoyloxy-4,5-deoxymaytansinol 3-isobutyrate A mixture of 15 mg of 20-demethoxy-20-hydroxy-4,5-deoxymaytansinol 3-isobutyrate and 9 μl of phenyl isocyanate in 1 ml of pyridine is stirred at room temperature overnight. The reaction mixture is worked up and purified as in Example 12, giving 8.9 mg of 20-demethoxy-20-N-phenylcarbomoyloxy-4,5-deoxymaytansinol 3-isobutyrate. Mass spectrum (m/e): 661, 543.

EXPERIMENTAL DATA

Antitumor activity

Therepeutic tests were carried out in mice according to NCI-protocol 1,300, Cancer Chemother. Reports, Part 3, 1972, Vol, 3, No. 2, in which melanoma B-16 tumor cells had been intraperitoneally transplanted, compound (I) being administered intraperitoneally once daily for 9 consecutive days. Life span prolongations obtained are shown in Table 1 as T/C % values.

TABLE 1

| Compound | Dose (μg/kg) | Antitumor activities B-16 (T/C %) |
|---|---|---|
| 4,5-deoxymaytansinol 3-isobutyrate | 100 | 216 |
| | 50 | 240 |
| | 25 | 175 |
| | 12.5 | 163 |

What is claimed is:

1. A compound of the formula:

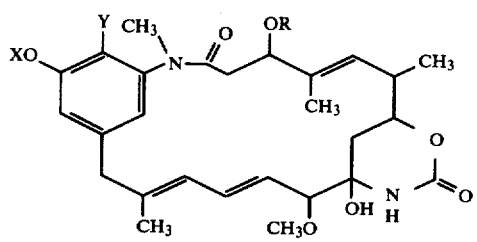

wherein

X is hydrogen, $C_{1-8}$ alkyl which is unsubstituted or substituted with halogen, carboxyl, $C_{2-5}$ alkoxycarbonyl, phenoxycarbonyl, $C_{1-4}$ alkoxy, benzyloxy, $C_{1-4}$ alkylthio, benzylthio, phenylthio, $C_{1-4}$ alkylsulfinyl, benzylsulfinyl, phenylsulfinyl, $C_{1-4}$ alkylsulfonyl, benzylsulfonyl, phenylsulfonyl, $C_{1-5}$ alkanoyloxy, benzoyloxy, phenylacetyloxy, cyano, di($C_{1-4}$alkyl)amino, oxo, ($C_{1-4}$)-1-alkylidene, phenyl, α- or β-naphthyl, vinyl, ethynyl, $C_{3-6}$ cycloalkyl, pyridyl, pyrimidyl, pyrazinyl, pyridazinyl, triazinyl, piperidinyl, piperazinyl, pyrrolyl, pyrrolidinyl, pyrrolinyl, imidazolyl, pyrazolyl, triazolyl, tetrazolyl, imidazolinyl, pyrazolidinyl, imidazolidinyl, triazolidinyl, furyl, furanyl, tetrahydrofuryl, thienyl, morpholino, oxazolyl, oxazolinyl, thiazolyl, thiazolinyl, oxadiazolyl, thiadiazolyl, oxiranyl, dioxolanyl or/and dithiolanyl, or X is acyl derived from a $C_{1-20}$ carboxylic acid of the formula:

—COR$^1$ wherein R$^1$ is hydrogen, $C_{1-18}$ alkyl, $C_{2-10}$ alkenyl, $C_{3-10}$ cycloalkyl, $C_{3-10}$ cycloalkenyl, phenyl, naphthyl, any of said groups being unsubstituted or substituted by $C_{1-4}$ alkoxy, $C_{2-4}$ alkanoyl, $C_{2-4}$ alkanoyloxy, $C_{2-4}$ alkoxycarbonyl, halogen, hydroxyl, nitro, cyano, trifluoromethyl, amino, mono($C_{1-4}$ alkyl)amino, di($C_{1-4}$ alkyl)amino, $C_{1-4}$ alkylthio, $C_{1-4}$ alkylsulfinyl, $C_{1-4}$ alkanesulfonyl, oxo, thioxo or $C_{1-4}$ alkanoylamino, and said cycloalkyl, cycloalkenyl, phenyl and naphthyl being attached, directly or through $C_{1-4}$ alkylene, to the carbonyl radical in the acyl group, or X is of the formula:

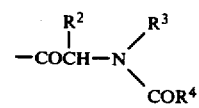

wherein

R$^2$ is hydrogen, $C_{1-18}$ alkyl, $C_{3-10}$ cycloalkyl, phenyl or naphthyl,

R$^3$ is hydrogen, $C_{1-18}$ alkyl, $C_{3-10}$ cycloalkyl, phenyl or naphthyl, and R$^4$ is hydrogen, $C_{1-18}$ alkyl, $C_{2-10}$ alkenyl, $C_{3-10}$ cycloalkyl, phenyl or naphthyl, any of said groups in R$^2$, R$^3$ and R$^4$ being unsubstituted or substituted by $C_{1-4}$ alkoxy, $C_{2-4}$ alkanoyl, $C_{2-4}$ alkanoyloxy, $C_{2-4}$ alkoxycarbonyl, halogen, hydroxyl, nitro, cyano, trifluoromethyl, amino, mono($C_{1-4}$ alkyl) amino, di($C_{1-4}$ alkyl) amino, $C_{1-4}$ alkylthio, $C_{1-4}$ alkylsulfinyl, $C_{1-4}$ alkanesulfonyl, oxo, thioxo or $C_{1-4}$ alkanoylamino, and said cycloalkyl, cycloalkenyl, phenyl and naphthyl in R$^2$, R$^3$ and R$^4$ being attached, directly or through $C_{1-4}$ alkylene, to the α-carbon atom, N-atom or the carbonyl group on the N-atom, or wherein X is acyl derived from an organic sulfonic acid of the formula:

—SO$_2$R$^5$ wherein

R$^5$ is $C_{1-4}$ alkyl or $C_{7-9}$ aralkyl or acyl derived from carbamic acid of the formula:

—CONR$^6$R$^7$ wherein

R$^6$ and R$^7$ are the same or different and each is hydrogen, $C_{1-6}$ alkyl, $C_{3-6}$ cycloalkyl, benzyl, phenethyl, phenyl or α- or β-naphthyl;

Y is hydrogen or chlorine; and

R is hydrogen or acyl derived from $C_{1-20}$ carboxylic acid of the formula:

—COR$^1$ wherein R$^1$ is the same as defined above, or R is of the formula:

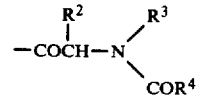

wherein R$^2$, R$^3$ and R$^4$ are the same as defined above.

2. A compound according to claim 1, wherein X is unsubstituted $C_{1-8}$ alkyl.

3. A compound according to claim 1, wherein R$^2$, R$^3$ and R$^4$ in the definition of radical R are each $C_{1-6}$ alkyl.

4. A compound according to claim 1, wherein X is hydrogen.

5. A compound according to claim 1, wherein Y is chlorine.

6. A compound according to claim 1, wherein R$^1$ is $C_{1-6}$ alkyl.

7. A compound according to claim 1, wherein R is hydrogen.

8. The compound according to claim 1, which is 4,5-deoxymaytansinol 3-isobutylate.

9. The compound according to claim 1, which is 4,5-deoxymaytansine.

10. The compound according to claim 1, which is 20-demethoxy-20-hydroxy-4,5-deoxymaytansinol 3-isobutylate.

11. A pharmaceutical composition for inhibiting the growth of tumor cells and prolonging the survival time of a warm-blooded animal which contains an effective amount of a compound of claim 4, 5, 6, 7, 8, 9, 10, 1, 2 or 3 and a pharmaceutically acceptable carrier, vehicle or diluent therefor.

12. A method for inhibiting the growth of tumor cells and prolonging the survival time of a warm-blooded animal, which comprises administering to said animal an effective amount of a compound of claim 4, 5, 6, 7, 8, 9, 10, 1, 2 or 3.

* * * * *